(12) United States Patent
Hegab et al.

(10) Patent No.: US 9,278,350 B1
(45) Date of Patent: Mar. 8, 2016

(54) METHOD AND DEVICES FOR PRODUCING MICRO-FLUIDS

(71) Applicant: KING ABDULAZIZ CITY SCIENCE & TECHNOLOGY (KACST), Riyadh (SA)

(72) Inventors: Hanaa Mohamed Samy Hegab, Adelaide (AU); Ahmed Mamdouh Mahmoud Elmekawy, Adelaide (AU)

(73) Assignee: King Abdulaziz City for Science and Technology (KACST), Riyadh (SA)

( * ) Notice: Subject to any disclaimer, the term of this patent is extended or adjusted under 35 U.S.C. 154(b) by 0 days.

(21) Appl. No.: 14/517,853

(22) Filed: Oct. 19, 2014

(51) Int. Cl.
*B01F 3/08* (2006.01)
*B01L 3/02* (2006.01)
*B01L 3/00* (2006.01)
*A61K 9/50* (2006.01)
*B01F 5/04* (2006.01)
*B01F 13/00* (2006.01)
*B01F 5/06* (2006.01)

(52) U.S. Cl.
CPC .............. *B01L 3/0241* (2013.01); *A61K 9/5089* (2013.01); *B01F 5/0471* (2013.01); *B01F 13/0069* (2013.01); *B01L 3/5025* (2013.01); *B01L 3/502707* (2013.01); *B01L 3/502784* (2013.01); *B01F 3/0811* (2013.01); *B01F 3/0865* (2013.01); *B01F 3/0869* (2013.01); *B01F 5/0661* (2013.01); *B01F 5/0682* (2013.01); *B01F 2215/0431* (2013.01); *B01L 3/50273* (2013.01); *B01L 3/502761* (2013.01); *B01L 2200/027* (2013.01); *B01L 2200/06* (2013.01); *B01L 2200/0668* (2013.01); *B01L 2200/0673* (2013.01); *B01L 2200/12* (2013.01); *B01L 2300/042* (2013.01); *B01L 2300/0838* (2013.01); *B01L 2300/0861* (2013.01); *B01L 2300/0864* (2013.01); *B01L 2300/12* (2013.01); *B01L 2400/0406* (2013.01); *Y10T 137/0329* (2015.04); *Y10T 137/2224* (2015.04)

(58) Field of Classification Search
None
See application file for complete search history.

*Primary Examiner* — Jill Warden
*Assistant Examiner* — Timothy G Kingan
(74) *Attorney, Agent, or Firm* — Timberline Patent Law Group PLLC

(57) ABSTRACT

The present application provides methods and devices for producing micro-fluids. Each device comprises a plurality of parallel inlet channels, an intersection and a plurality of parallel outlet channels. The plurality of parallel inlet channels comprises a first set of inlet channels for introducing a first fluid at a first flow rate, a second set of inlet channels for introducing a second fluid at a second flow rate and a third set of inlet channels for introducing a third fluid at a third flow rate. Once introduced, the first fluid, the second fluid and the third fluid flow through the corresponding channels to intersect at the intersection and form micro-fluids, which can be collected from the plurality of parallel outlet channels.

32 Claims, 9 Drawing Sheets

METHOD AND DEVICES FOR PRODUCING MICRO-FLUIDS

FIELD OF INVENTION

The present application generally relates to the field of microfluidics. More specifically, the present application relates to methods and devices for producing micro-fluids.

BACKGROUND OF THE INVENTION

Smaller micro-fluids offer several advantages such as, but not limited to, easier transportation, controlled dispersion, increased mechanical strength and easier injection. Therefore, the need for micro-fluids such as micron-sized polymeric beads with dimensions <100 micrometer (μm) is increasing. However, the size of microcapsules produced cannot be easily controlled, and the resulting beads tend to merge into larger beads before post processing. This considerably limits the application of such micro-fluids. For example, the major reason for the limited bioavailability of orally administered proteins is because of their restricted reproducibility, which can cause various drug packing capacity and different release kinetics.

Therefore, there is a need for improved methods and devices for producing micro-fluids.

BRIEF DESCRIPTION OF THE DRAWINGS

The accompanying figures wherein like reference numerals refer to identical or functionally similar elements throughout the separate views and which together with the detailed description below are incorporated in and form part of the specification, serve to further illustrate various embodiments and to explain various principles and advantages all in accordance with the present application.

FIGS. 1-5 illustrate various views of a microfluidic device, or components thereof, in accordance with an embodiment of the present application, wherein:

FIGS. 1, 3, 4 and 5 illustrate simplified perspective and cross-sectional views of the microfluidic device; and FIG. 2 illustrates a simplified perspective view of a mobile comb structure of the microfluidic device.

DETAILED DESCRIPTION OF THE INVENTION

Figure 1:
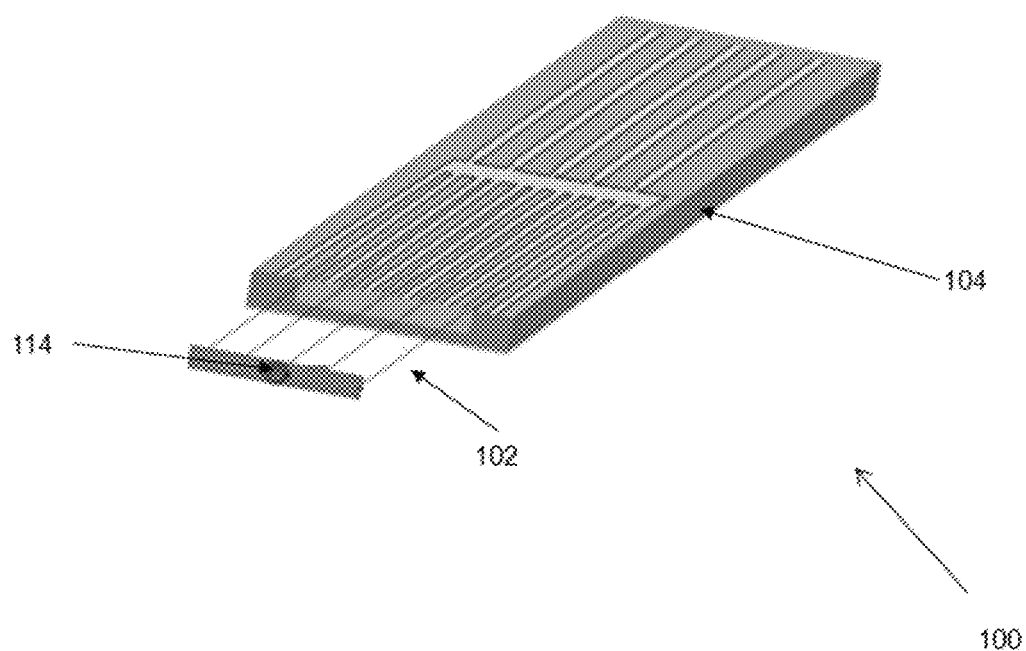

Before describing in detail embodiments that are in accordance with the invention, it should be observed that the embodiments reside primarily in method steps and device components related to methods and devices for producing micro-fluids. Accordingly, the device components and method steps have been represented where appropriate by conventional symbols in the drawings, showing only those specific details that are pertinent to understanding the embodiments of the present application so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any such actual relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Generally speaking, various embodiments of the present application provide methods and devices for producing micro-fluids.

The term "micro-fluids" as used herein refers to fluids having a diameter of about 1 millimeter (mm) or less. However, it should be apparent that the term "micro-fluids" may be used to refer to fluids having slightly lesser or higher diameters.

Various types of micro-fluids such as, but not limited to, droplets, oils and polymeric micro-beads, can be produced using the methods and devices disclosed herein.

For example, the methods and devices can be used for producing polymeric micro-beads, which find applications in one or more of, but not limited to, cell encapsulation, adhesives, carbonless copy papers, e-papers or e-inks, essential oils, pesticides and herbicides, phase change materials, powder perfumes, scratch-n-sniffs, self-healing materials, textiles, temperature release in baking, thermochromic dyes, time release technology for pharmaceuticals and visual indicators.

In accordance with the various embodiments, each device for producing micro-fluids comprises a plurality of parallel inlet channels. The plurality of parallel inlet channels comprises a first set of inlet channels for injecting a first fluid at a first flow rate; a second set of inlet channels for injecting a second fluid at a second flow rate; and a third set of inlet channels for injecting a third fluid at a third flow rate. The channels of the first set of inlet channels are generally nested within the channels of the second set of inlet channels. Alternately, the channels of the first set of inlet channels can be arranged between channels of the second set of inlet channels. Moreover, channels of the second set of inlet channels are generally enclosed between two adjacent channels of the third set of inlet channels. Further, channels of the third set of inlet channels are generally disposed at one of an end of the plurality of parallel inlet channels, adjacent to one another and between two adjacent channels of the second set of inlet channels.

Each device further comprises an intersection. The channels of the plurality of inlet channels are designed such that the channels meet at the intersection. Accordingly, the first fluid, the second fluid and the third fluid can separately flow through the plurality of parallel inlet channels and intersect at the intersection to form micro-fluids.

In addition, each device comprises a plurality of parallel outlet channels for collecting the micro-fluids.

There could be numerous variations related to the plurality of parallel inlet channels, the intersection and/or the plurality of parallel outlet channels. For example, different parameters can be employed for determining the number of channels/intersection, the shape of channels and/or intersection, the dimension of the channels and/or intersection, the gap between the channels, the arrangement of the channels/intersection and so forth.

Further, there could be numerous variations related to the type of fluids that can be used. In addition, there could be numerous variations in the manner of injecting the fluids through the channels. For instance, fluids could be injected through common or separate inlets and at similar or different flow rates.

Reference will now be made to FIGS. 1-5, which illustrate a microfluidic device 100, or components thereof, in accordance with an embodiment of the present application.

Microfluidic device 100 can be used for producing microfluids. Microfluidic device 100 can have a desired shape and dimension. For example, microfluidic device can have a rectangular cross-section and a length:breadth:height ratio of 6:3:0.5. The shape/dimension of microfluidic device 100 can be determined based on one or more parameters such as, but not limited to, type of micro-fluids to produce, desired production rate, flow rates and fabrication technique used.

Microfluidic device 100 comprises a mobile comb structure 102, a wafer 104 and a cover 106.

Mobile comb structure 102 can be used to inject a first fluid at a first flow rate for producing micro-fluids. For example, mobile comb structure 102 can be used for injecting a core or sample at a flow rate of F µL/min, wherein F is a positive integer. Accordingly, the first flow rate can be, but need not be limited to, 1 µL/min, 3 µL/min and 7 µL/min. The first fluid can be determined based on the type of micro-fluids being produced. Further, the first flow rate can be determined based on one or more parameters such as, but not limited to, desired production rate, type of micro-fluids to produce and first fluid characteristics.

Mobile comb structure 102 can have a desired length:breadth:height ratio. For example, the length of mobile comb structure 102 can be 1.5X mm, the breadth of mobile comb structure can be 3X mm, and the height of mobile comb structure 102 can be 0.25X mm, wherein X is a positive integer.

Figure 2:
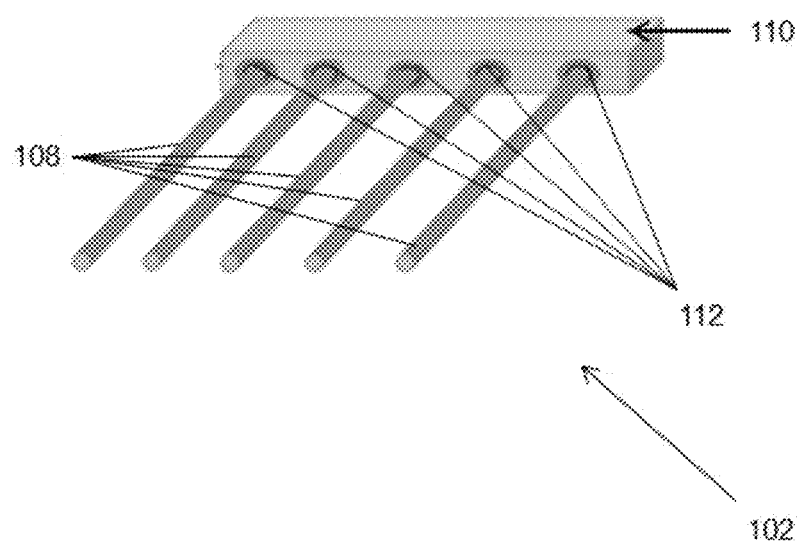

Mobile comb structure 102 comprises a first set of inlet channels 108 (hereafter first set 108), a fluid routing component 110, and unions and fittings 112 as illustrated in FIG. 2.

First set 108 comprises parallel channels for introducing the first fluid. Further, first set 108 can have a desired number of channels (N). For example, the number of channels in first set 108 can be five as illustrated in FIG. 2. The number of channels in first set 108 can be determined based on one or more parameters such as, but not limited to, desired production rate, flow rate, and first fluid characteristics.

Each channel of first set 108 can have a desired shape for introducing the first fluid. For example, each channel can be cylindrical as illustrated in FIG. 2. Alternately, each channel can be rectanguloidal or paralleloidal in shape. Further, each channel can be made from an appropriate material. For instance, each channel can be a Polyether Ether Ketone (PEEK) capillary tube.

In addition, each channel of first set 108 can have a desired dimension. For example, each channel can have an inner diameter in the range of 1X µm to 3X µm and an outer diameter in the range of 3X µm to 6X µm, wherein X is a positive integer. For example, the inner and outer diameter of each channel can be 1 µm and 5 µm respectively. Similarly, each channel of first set 108 can have a length of 1.2X mm as illustrated in FIG. 2, wherein X is a positive integer. For example, each channel can have a length of 1.2 mm. The shape/dimensions of each channel of first set 108 can be determined based on one or more parameters such as, but not limited to, desired production rate, flow rates, type of microfluids to produce and first fluid characteristics.

First set 108 can be connected with fluid routing component 110 to enable the introduction of the first fluid. The connection can be established by using unions and fittings 112. For example, NanoTight™ unions and fittings can be used for connecting first set 108 with fluid routing component.

Fluid routing component 110 can be of a desired shape for facilitating connection of first set 108 and for facilitating introduction of the first fluid at the first flow rate. For example, fluid routing component 110 can be box-shaped.

Further, fluid routing component 110 can have one or more inlets for introducing the first fluid at the first flow rate. For example, first set 108 can be connected to an inlet 114 of fluid routing component 110 as illustrated in FIG. 1 for introducing the first fluid at the first flow rate.

Each of the one or more inlets can have a desired shape/dimension. For example, a diameter of inlet 114 can be 0.8X mm, wherein X is a positive integer. The shape/dimension of inlet 114 can be determined based on one or more parameters such as, but not limited to, type of fluid being injected, flow rate and desired production rate.

It should be noted that channels of first set 108 can have a common or separate inlets. Further, such inlets may also be provided directly on the channels in lieu of providing the inlets on a separate component. In other words, fluid routing component 110 may not be present as a separate component and each channel of first set 108 can have an inlet or all channels of first set 108 can have a common inlet.

In order to introduce the first fluid for producing micro-fluids, mobile comb structure 102 can be moved relative to wafer 104 in order to appropriately integrate mobile comb structure 102 with respect to wafer 104. This also enables replacing mobile comb structure 102 with another similar mobile comb structure. Such replacement enables dynamic control over the production of micro-fluids.

Figure 3:
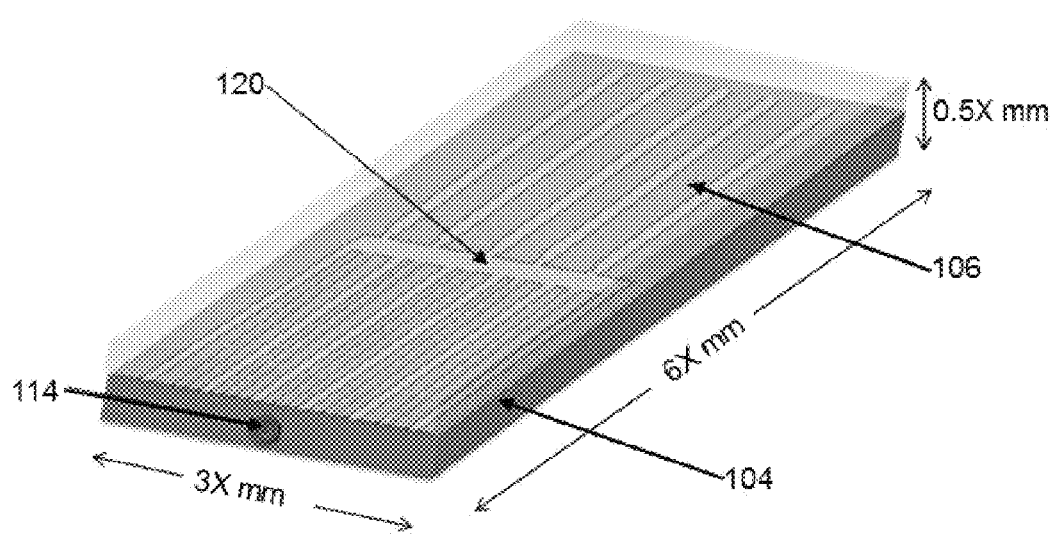

Wafer 104 of microfluidic device 100 can be made from silicon or any other suitable material. Wafer 104 can have a desired dimension. For example, ratio of length:breadth:height of microfluidic device 100 can be 6:3:0.25 as illustrated in FIG. 3. The dimensions of wafer 104 can be determined based on one or more parameters such as, but not limited to, fabrication technique used, production rate, flow rates and type of fluids/micro-fluids.

Figure 4:
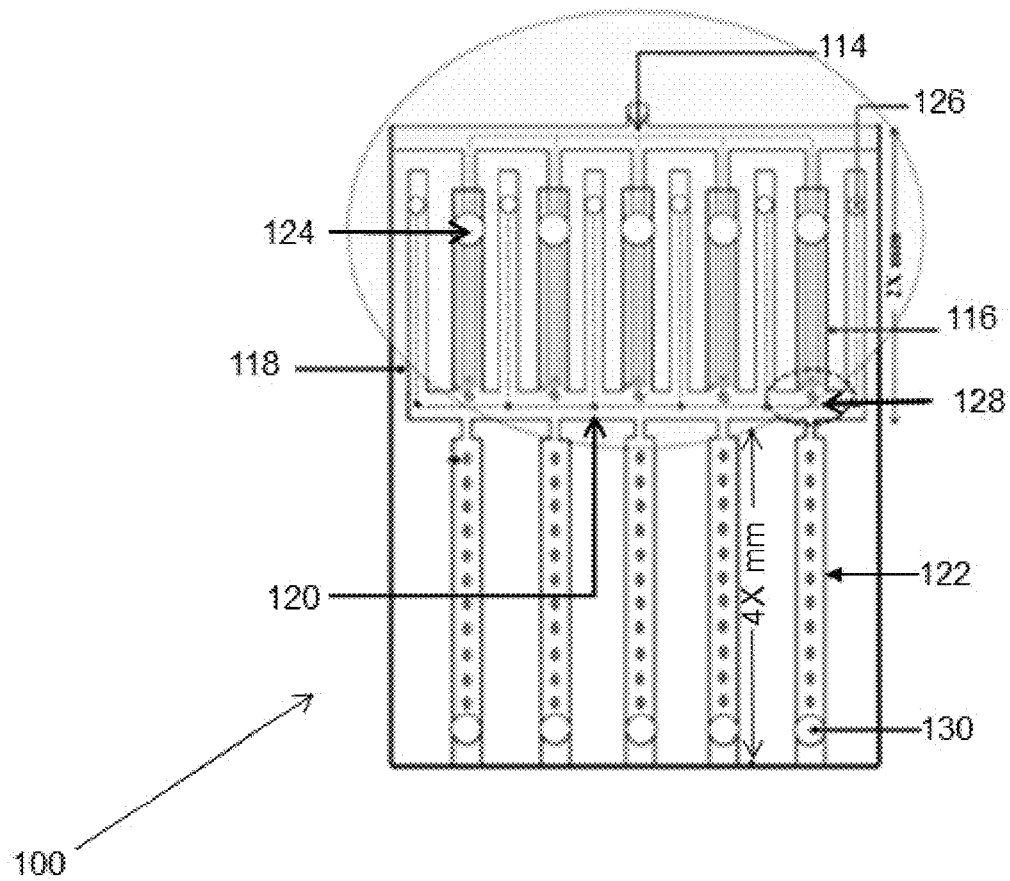

As illustrated in FIG. 4, wafer 104 comprises a second set of inlet channels 116 (hereafter second set 116), a third set of inlet channels 118 (hereafter third set 118), an intersection 120, and a plurality of parallel outlet channels 122, each of which can be created on wafer 104 using one or more techniques such as, but not limited to, deep reactive ion etching. Further, each can be created on wafer 104 in a single-go (in one attempt) or separately.

Second set 116 can have parallel channels as shown in FIG. 4 for introducing a second fluid at a second flow rate. For example, second set 116 can be used for injecting a shell or a polymer at a flow rate of 2F µL/min, wherein F is a positive integer. Accordingly, the second flow rate can be, but need not be limited to, 2 µL/min, 4 µL/min, 8 µL/min and 12 µL/min. The second fluid can be determined based on one or more parameters such as the type of micro-fluid being produced. Further, the second flow rate can be determined based on one or more parameters such as, but not limited to, desired production rate, flow rates, type of micro-fluids to produce and second fluid characteristics.

Second set 116 can be designed such that channels of first set 108 can be appropriately aligned for producing micro-fluids as illustrated in FIG. 4. For example, as illustrated in FIGS. 1 and 4, second set 116 is created on wafer 104 such that each channel of first set 108 can be moved relative to a corresponding channel of second set 116 in order to coaxially align channels of first set 108 with channels of second set 116. In the coaxial alignment, each channel of first set 108 is enclosed within a corresponding channel of second set 116 as illustrated in FIG. 4.

Second set 116 can have a desired number of channels (N). For example, the number of channels of second set 116 can be five as illustrated in FIG. 4. The number of channels of second set 116 can be determined based on one or more parameters such as, but not limited to, desired production rate, flow rate, type of micro-fluids to produce and second fluid characteristics.

Further, each channel of second set 116 can have a desired shape for introducing the second fluid. For example, each channel can be cylindrical. Alternately, each channel can be rectanguloidal or paralleloidal in shape. Further, each channel can be made from an appropriate material.

In addition, each channel of second set 116 can have a desired dimension. For example, each channel of second set 116 can have a length of X to 2X mm, a width 7X to 10X μm and a height of 0.25 to 0.5X μm, wherein X is a positive integer.

The shape/dimensions of each channel of second set 116 can be determined based on one or more parameters such as, but not limited to, desired production rate, flow rate, type of micro-fluids to produce and second fluid characteristics.

Figure 5:
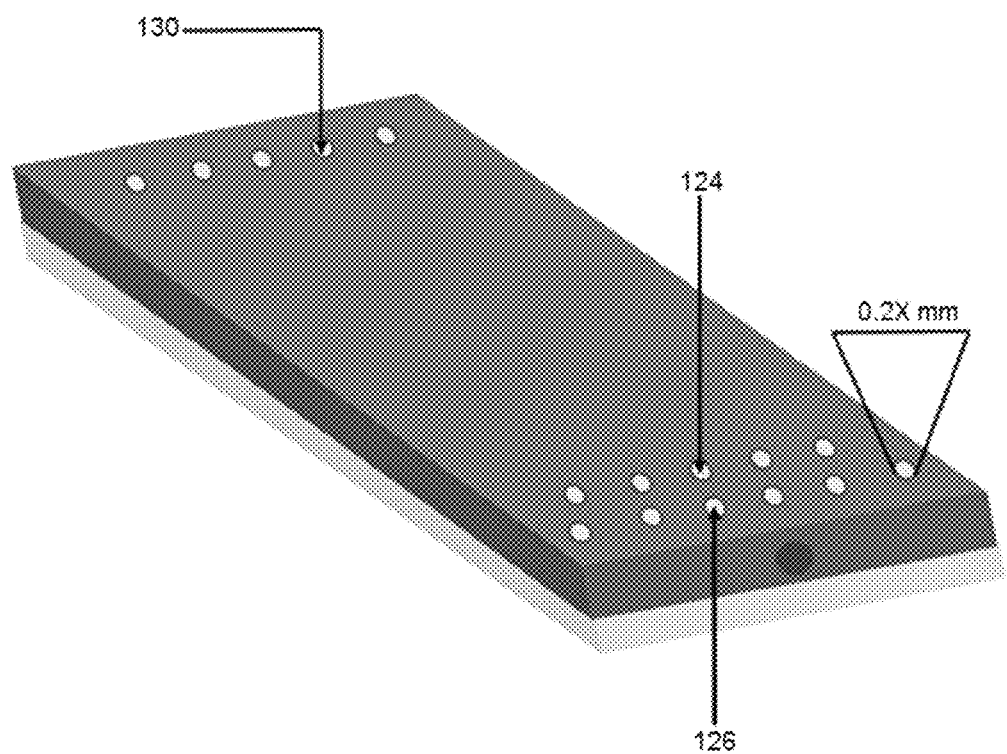

Additionally, each channel of second set 116 can have separate inlets for introducing the second fluid at the second flow rate as illustrated in FIG. 4 and FIG. 5. The inlets of second set 116 can be created by drilling corresponding holes on wafer 104. Further, each inlet can have a desired shape/dimension. For example, the diameter of inlet 124 can be 0.007X to 0.01X mm, wherein X is a positive integer. The shape/dimensions can be determined based on one or more parameters such as, but not limited to, desired production rate, flow rate, type of micro-fluids to produce and type of fluids being introduced. It will be apparent to those ordinarily skilled in the art that channels of second set 116 can also have a common inlet.

Each channel of second set 116 can be arranged between two adjacent channels of third set 118 as illustrated in FIG. 4.

Third set 118 can have parallel channels as shown in FIG. 4 for introducing a third fluid at a third flow rate. For example, third set 118 can be used for injecting a cross-linker at a flow rate of 3F μL/min, wherein F is a positive integer. Accordingly, the third flow rate can be, but need not be limited to, 3 μL/min, 9 μL/min, 18 μL/min and 27 μL/min. The third fluid can be determined based on one or more parameters such as the type of micro-fluid being produced. Further, the third flow rate can be determined based on one or more parameters such as, but not limited to, desired production rate, flow rate, type of micro-fluids to produce and third fluid characteristics.

Third set 118 can have a desired number of channels (N+1). For example, the number of channels of third set 118 can be six as illustrated in FIG. 4. The number of channels of third set 118 can be determined based on one or more parameters such as, but not limited to, desired production rate, flow rate, type of micro-fluids and third fluid characteristics.

Further, each channel of third set 118 can have a desired shape for introducing the third fluid. For example, each channel can be cylindrical. Alternately, each channel can be rectanguloidal or paralleloidal in shape. Further, each channel can be made from an appropriate material.

In addition, each channel of third set 118 can have a desired dimension. For example, each channel of third set 118 can have a length of X to 2X mm, a width of 4X to 9X μm and a height of 0.25X to 0.5X μm, wherein X is a positive integer.

The shape/dimensions of each channel of third set 118 can be determined based on one or more parameters such as, but not limited to, desired production rate, flow rate, type of micro-fluids to produce and third fluid characteristics.

Additionally, each channel of third set 118 can have separate inlets for introducing the third fluid at the third flow rate as illustrated in FIG. 4 and FIG. 5. The inlets of third set 118 can be created by drilling corresponding holes on wafer 104. Further, each inlet can have a desired shape/dimension. For example, diameter of inlet 126 can be 0.004X to 0.009X mm, wherein X is a positive integer. It will be apparent to those ordinarily skilled in the art that channels of third set 118 can also have a common inlet.

The shape/dimensions of the one or more inlets can be determined based on one or more parameters such as, but not limited to, desired production rate, flow rate, type of micro-fluids to produce and third fluid characteristics.

Each channel of third set 118 can be located at an end as illustrated in FIGS. 1, 3 and 4. Alternately, each channel of third set 118 can be located between two adjacent channels of second set 116.

As illustrated in FIG. 4, each channel of second set 116 and third set 118 can be designed to end at intersection 120.

Intersection 120 is disposed on wafer 104 for facilitating intersection of the first fluid, the second fluid and the third fluid for formation of micro-fluids. Intersection 120 can have a desired shape. For example, intersection 120 can have a rectangular cross section as shown in FIG. 4. Such a rectangular cross-section provides a plurality of T-junctions 128 as illustrated in FIG. 4. Plurality of T-junctions 128 facilitates formation of micro-fluids due to one or more principles such as gelation.

The shape of intersection 120 can be based on one or more parameters such as, but not limited to, channel characteristics, desired production rate, flow rates, type of micro-fluids to produce and characteristics of the first, second and third fluids.

Intersection 120 can have a desired dimension. For example, intersection 120 can have a length of 0.1X to 0.8X mm, a width of 2.5X to 3X mm and a height of 0.25X to 0.5X μm, wherein X is a positive integer.

The dimension of intersection 120 can be determined based on one or more parameters such as, channel characteristics, desired production rate, flow rates, type of micro-fluids to produce and characteristics of the first, second and third fluids.

As illustrated in FIG. 4, plurality of parallel outlet channels 122 of wafer 104 originate from intersection 120, thereby facilitating collection of micro-fluids that can be formed at intersection 120.

There could be a desired number of channels in plurality of parallel outlet channels 122 (N). For example, the number of channels can be five as illustrated in FIG. 4. The number of channels in plurality of parallel outlet channels 122 can be determined based on one or more parameters such as, but not limited to, characteristics of inlet channels, characteristics of intersection 120, desired production rate, flow rates and types of micro-fluids to produce.

Further, each channel of plurality of parallel outlet channels 122 can have a desired shape for collecting the micro-fluids. For example, each channel can be cylindrical. Alternately, each channel can be rectanguloidal or paralleloidal in shape. Further, each channel can be made from an appropriate material.

In addition, each channel of plurality of parallel outlet channels 122 can have a desired dimension. For example, each channel of plurality of parallel outlet channels 122 can have a width of 7X to 10X μm, wherein X is a positive integer. Further, each channel of plurality of parallel outlet channels 122 can have a length of 4X to 8X mm, wherein X is a positive integer. In addition, each channel of plurality of parallel outlet channels 122 can have a height of 0.25X to 0.5X μm.

Moreover, each channel of plurality of parallel outlet channels 122 can have two widths as illustrated in FIG. 4, wherein the first width can be 2X to 3X μm, while the second width can be 7X to 10X μm.

The shape/dimensions of each channel of plurality of parallel outlet channels 122 can be determined based on one or more parameters such as, but not limited to, characteristics of inlet channels, characteristics of intersection 120, desired production rate, flow rates and type of micro-fluids to produce.

Plurality of parallel outlet channels 122 comprises one or more outlets for collecting micro-fluids. For example, plurality of parallel outlet channels 122 can have one common outlet. Alternately, each of plurality of parallel outlet channels 122 can have an outlet such as 130 as illustrated in FIG. 4 and FIG. 5. The one or more outlets can be created by drilling corresponding holes on wafer 104. Further, each outlet can have a desired shape/dimension. For example, a diameter of outlet 130 can be 0.007X to 0.01X mm, wherein X is a positive integer.

Cover 106 of microfluidic device can enclose mobile comb structure 102 and wafer 104 in order to facilitate production of micro-fluids. Cover 106 can be bonded on wafer 104 using one or more methods well known in the art. For example, cover 106 can be anodically bonded on wafer 104.

The type of material used for preparing cover 106 can be determined based on one or more parameters, such as, but not limited to, desired characteristics of microfluidic device and desired visibility for fluid flows and micro-fluid formation. Accordingly, if visibility is desired, a material such as glass can be used for preparing cover 106 as illustrated in FIG. 3.

The shape/dimensions of cover 106 can be similar to that of wafer 104. Alternatively, cover 106 can have other suitable shape/dimensions.

Microfluidic device 100 can be utilized for producing various types of micro-fluids.

Figure 6:
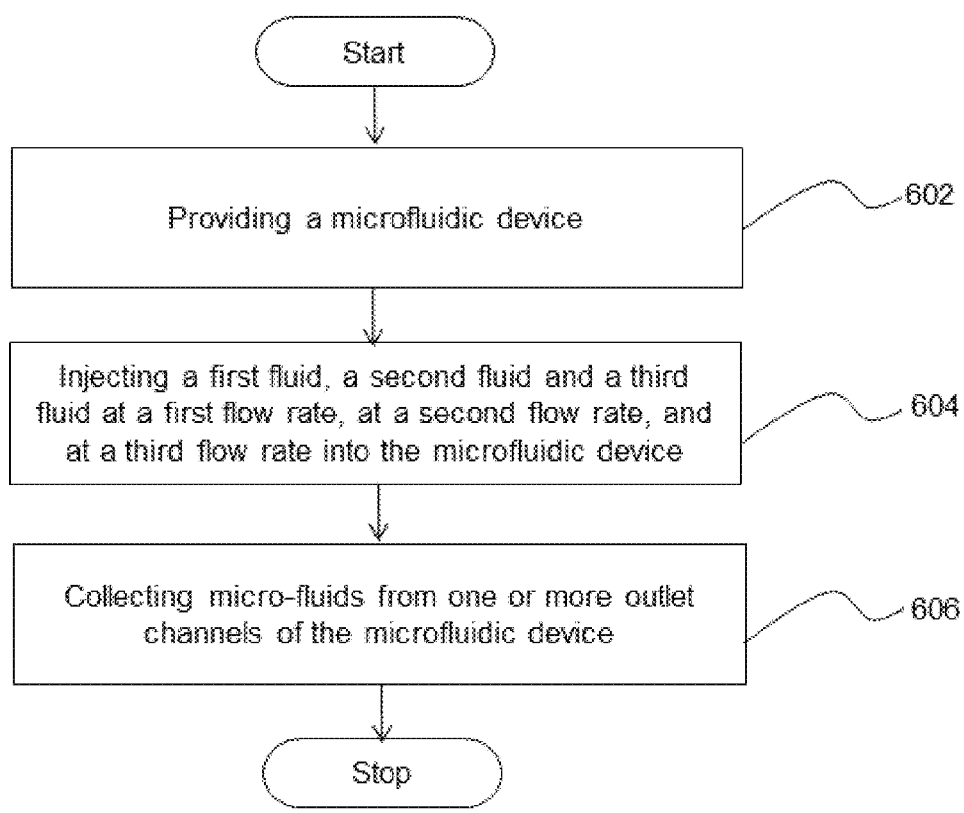
FIG. 6 illustrates a flow chart of a method for producing micro-fluids in accordance with an embodiment of the present application.

FIG. 6 illustrates a flow chart of a method for producing micro-fluids in accordance with an embodiment of the present application.

At 602, microfluidic device 100 is provided for producing micro-fluids. Providing microfluidic device 100 can include one or more of, but not limited to, fabricating microfluidic device 100 (described in detail in conjunction with description of FIG. 6) and utilizing a pre-fabricated microfluidic device 100. In addition, providing microfluidic device 100 comprises determining a configuration of microfluidic device 100. The configuration of microfluidic device 100 can be determined based on one or more parameters such as, but not limited to, type of micro-fluids to produce, characteristics of the first, second and third fluids, flow rates and desired production rate. Further, determining the configuration can include determining one or more of, but not limited to, material, shape, number and dimension of microfluidic device 100 or components thereof.

Providing microfluidic device 100 can also include substituting mobile comb structure 102 of microfluidic device 100 with a similar mobile comb structure. For example, if a mobile comb structure having first set 108 of a different inner diameter is required, it can be readily provided by substituting mobile comb structure 102.

At 604, a first fluid, a second and a third fluid are injected into first set 108, second set 116 and third set 118 respectively. Here, the first fluid, the second fluid and the third fluid are injected via one or more inlets of first set 108, second set 116 and third set 118 respectively.

The first fluid, the second fluid and the third fluid to inject can be determined based on the type of micro-fluids to produce. For example, to produce core-shell controlled mono-dispersed micro-fluids, the first fluid injected can be a core, the second fluid injected can be a polymeric shell and the third fluid injected can be a cross-linker. In accordance with the example, the core can be one of, but not limited to, drugs, lipids, adhesives, pesticides essential oils, materials and dyes. Further, the polymeric shell can be one of, but not limited to, polymers containing 3-hydroxy valerate and its derivatives, cellulose and its derivatives, polymers containing 3-hydroxy butyrate and its derivatives, agarose and its derivatives, starch derivatives, alginate and its derivatives, pectin and its derivatives and chitosan and its derivatives. In addition, the cross-linker can be one of, but not limited to, calcium chloride, sodium tripolyphosphate, glutaraldehyde, ethylene glycol diglycidyl ether, imidoester cross-linker dimethyl suberimidate, N-Hydroxysuccinimide-ester cross-linker BS3 and formaldehyde. It will be apparent that the examples listed above are merely representative and numerous other types of cores, shells and cross-linkers can be utilized for preparing core-shell micro-fluids.

The first fluid, the second fluid and the third fluid are injected at a first flow rate, a second flow rate and at a third flow rate respectively. The flow rates of the first fluid, the second fluid and the third fluid can be determined based on one or more parameters such as, but not limited to, desired production rate, channel characteristics, fluid characteristics and type of micro-fluids to produce.

It should be apparent that the flow rates of any of the first fluid, the second fluid and the third fluid can be adjusted dynamically to obtain a desired output. Further, the flow rates can be identical or different.

Injecting the first fluid, the second fluid and the third fluid (hereafter referred to as three fluids) causes the three fluids to flow separately through the corresponding channels and intersect at intersection 120 and produce micro-fluids. The production of micro-fluids can be governed by one or more parameters such as, but not limited to, fluid characteristics, flow rates, channel characteristics and intersection characteristics.

Assuming microfluidic device 100 is utilized for producing core-shell controlled mono-dispersed micro-beads and has a configuration as illustrated in FIG. 3. In this configuration, intersection 120 facilitates the initial gelation, wherein the core firstly meets the shell to produce core-shell particles. The core-shell particles then get initially cross-linked at plurality of T-junctions 128 to produce micro-beads. Gelation arises when the polymer drop comes into contact with the solution of the cross linker divalent ions and continues until the physical cross linking of the whole micro-fluids, where divalent ions diffusion occurs from the continuous phase across the boundary of the drop.

The micro-fluids produced at intersection 120 flow out through plurality of parallel outlet channels 122. It would be apparent that the characteristics of the channels and the intersection can affect the production of the micro-fluids. In accordance with the above example of core-shell controlled mono-dispersed micro-beads, the configuration of first set 108, second set 116, third set 118, intersection 120 and plurality of parallel outlet channels 122 causes the micro-beads to be core-shell controlled and mono-dispersed.

At 606, the micro-fluids are collected through plurality of parallel outlet channels 122 of microfluidic device 100. The micro-fluids can be collected through one or more outlets of plurality of parallel outlet channels 122.

Microfluidic device 100 can be fabricated using various techniques.

Figure 7:
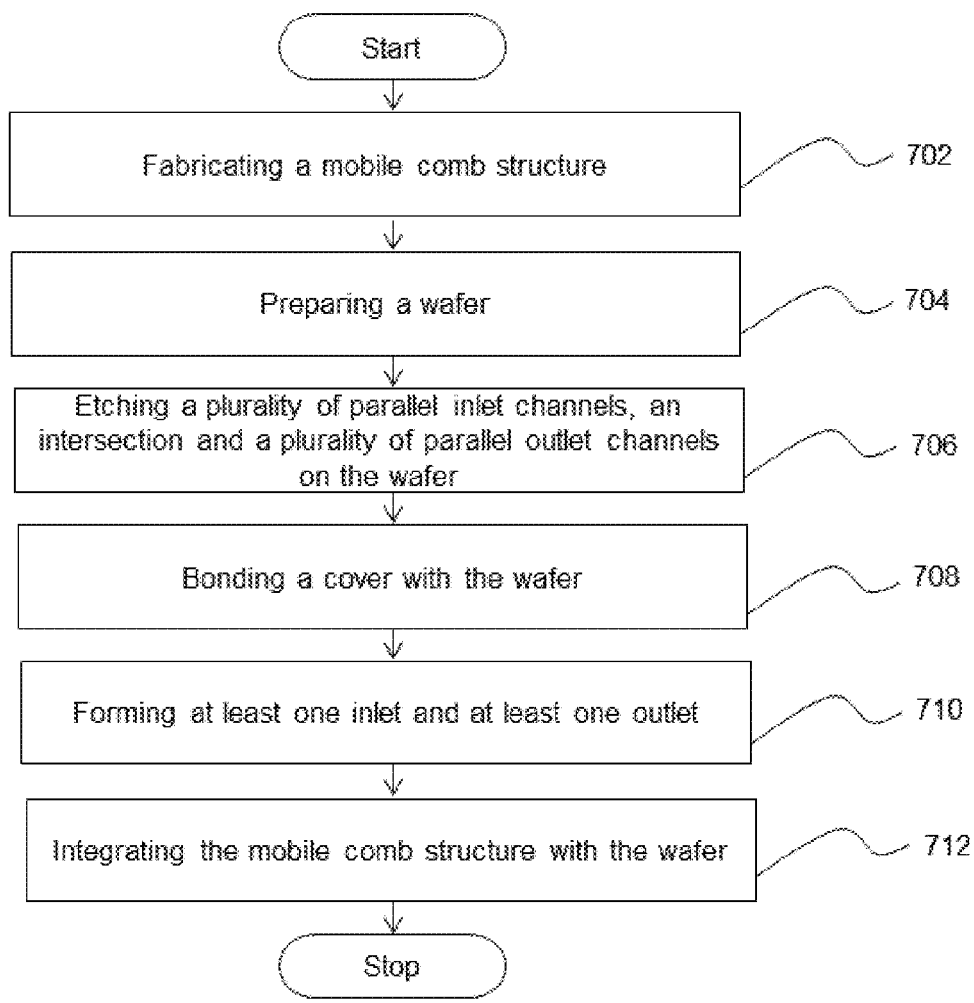
FIG. 7 illustrates a flow chart of a method for fabricating a microfluidic device in accordance with an embodiment of the present application.

FIG. 7 illustrates a flow chart of a method for fabrication of microfluidic device 100 in accordance with an embodiment of the present application.

At 702, mobile comb structure 102 is fabricated such that mobile comb structure 102 comprises a first set of inlet channels. The first set of inlet channels described herein in FIG. 7 can be considered to be equivalent to first set 108 of microfluidic device 100 described in detail in conjunction with description of FIGS. 1-5.

The channels of the first set of inlet channels are parallel to each other. The first set of inlet channels is configured to move relative to a second set of inlet channels on wafer 104 (described hereinafter) so as to coaxially align the first set of inlet channels with the second set of inlet channels for producing micro-fluids. In the coaxial alignment (refer FIG. 4), each channel of the first set of inlet channels is enclosed within a corresponding channel of the second set of inlet channels and each channel of the first set of inlet channels terminates at the intersecting region.

Fabricating mobile comb structure 102 comprises forming the first set of inlet channels connected to a fluid routing component such as fluid routing component 110. Here, the first set of inlet channels is attached to fluid routing component 110 by using unions and fittings 112. For example, NanoTight™ unions and fittings can be used for connecting the first set of inlet channels with fluid routing component 110.

Fluid routing component 110 can have one or more inlets (described in detail in conjunction with description of FIGS. 1-5). Further, the one or more inlets can be formed based on one or more parameters such as, but not limited to, desired flow rate, desired production rate, type of micro-fluids to produce and first fluid characteristics.

Forming the one or more inlets comprises determining the number of inlets and the location of the corresponding inlets. In addition, forming the one or more inlets comprises determining one or more of, a shape and a dimension of the one or more inlets.

Mobile comb structure 102 is fabricated based on one or more parameters such as, but not limited to, desired characteristics of the first set of inlet channels and fluid routing component 110.

At 704, wafer 104 is prepared. Preparing wafer 104 can include selecting one or more wafer characteristics such as, but not limited to, shape, dimension and material of wafer 104. The one or more wafer characteristics can be determined based on one or more of, but not limited to, type of micro-fluids to produce, desired production rate, flow rates and desired micro-fluid characteristics.

At 706, a plurality of parallel inlet channels, an intersection and a plurality of parallel outlet channels are etched on wafer 104.

The plurality of parallel inlet channels comprises a second set of inlet channels for introducing a second fluid at a second flow rate. The second set of inlet channels described herein in FIG. 7 can be considered to be equivalent to second set 116 of microfluidic device 100 described in detail in conjunction with description of FIGS. 1-5.

The plurality of parallel inlet channels further comprises a third set of inlet channels for introducing a third fluid at a third flow rate. The third set of inlet channels described herein in FIG. 7 can be considered to be equivalent to third set 118 of microfluidic device 100 described in detail in conjunction with description of FIGS. 1-5.

Further, each inlet channel of the second set of inlet channels is enclosed between inlet channels of the third set of inlet channels as would be readily apparent based on the description of FIGS. 1-5.

The intersection is etched such that the intersection is disposed at an end of the plurality of parallel inlet channels as intersection 120. Accordingly, the intersection is configured to facilitate formation of micro-fluids.

The plurality of parallel outlet channels originates from the intersection such as plurality of parallel outlet channels 122. Accordingly, the plurality of parallel outlet channels is configured to facilitate collection of the micro-fluids.

The plurality of parallel inlet channels, the intersection and the plurality of parallel outlet channels are etched using deep reactive ion etching or other suitable etching techniques. Further, the plurality of parallel inlet channels, the intersection and the plurality of parallel outlet channels can be etched together or in separate runs.

The etching can be performed based on one or more parameters such as, but not limited to, desired shape, number, dimension and/or material of the plurality of parallel inlet channels, the intersection and the plurality of parallel outlet channels.

At 708, cover 106 is bonded on to wafer 104. Cover 106 is bonded such that cover 106 can enclose mobile comb structure 102 and wafer 104 for producing micro-fluids.

Cover 106 can be anodically bonded on wafer 104. Alternately, any other suitable bonding technique can be utilized for bonding cover 106.

Cover 106 is bonded on wafer 104 based on one or more cover characteristics such as, but not limited to, shape, dimension and material of cover 106. The material of cover 106 can be glass to permit visibility during one or more of, alignment of mobile comb structure 102 and production of micro-fluids.

At 710, one or more inlets and one or more outlets are formed on wafer 104. The one or more inlets and the one or more outlets can be formed on the backside of wafer 104 as illustrated in FIG. 5. Further, the one or more inlets and the one or more outlets can be formed by drilling.

The one or more inlets are formed such that each of the second set of inlet channels (i.e. second set 116) and the third set of inlet channels (i.e. third set 118) comprises one or more inlets (described in detail in conjunction with description of FIGS. 1-5).

Further, the one or more inlets are formed based on one or more parameters such as, but not limited to, shape, dimension and material of wafer 104, desired flow rates, desired production rate and type of micro-fluids.

Forming the one or more inlets comprises determining the number of inlets for each of the second set of inlet channels (i.e. second set 116) and the third set of inlet channels (i.e. third set 118) and the location of the corresponding inlets. In addition, forming the one or more inlets comprises determining one or more of, a shape and a dimension of the one or more inlets.

The one or more outlets are formed such that each of the plurality of parallel outlet channels (i.e. plurality of parallel outlet channels 122) comprises one or more outlets (described in detail in conjunction with description of FIGS. 1-5). The process of forming the one or more outlets is similar to that of forming the one or more inlets. Here, the parameters to determine can be, but are not limited to, number, shape, dimension and location of the outlets.

At 712, mobile comb structure 102 is integrated with wafer 104 for producing micro-fluids. Here, mobile comb structure 102 can be moved relative to wafer 104 in order to appropriately integrate the first set of inlet channels (i.e. first set 108) of mobile comb structure 102 with respect to the second set of inlet channels (i.e. second set 116) of wafer 104.

This movement also enables removing mobile comb structure 102 completely from microfluidic device 100 and replacing mobile comb structure 102 with a similar mobile comb structure. Such replacement enables dynamic control over the production of micro-fluids.

Figure 8:
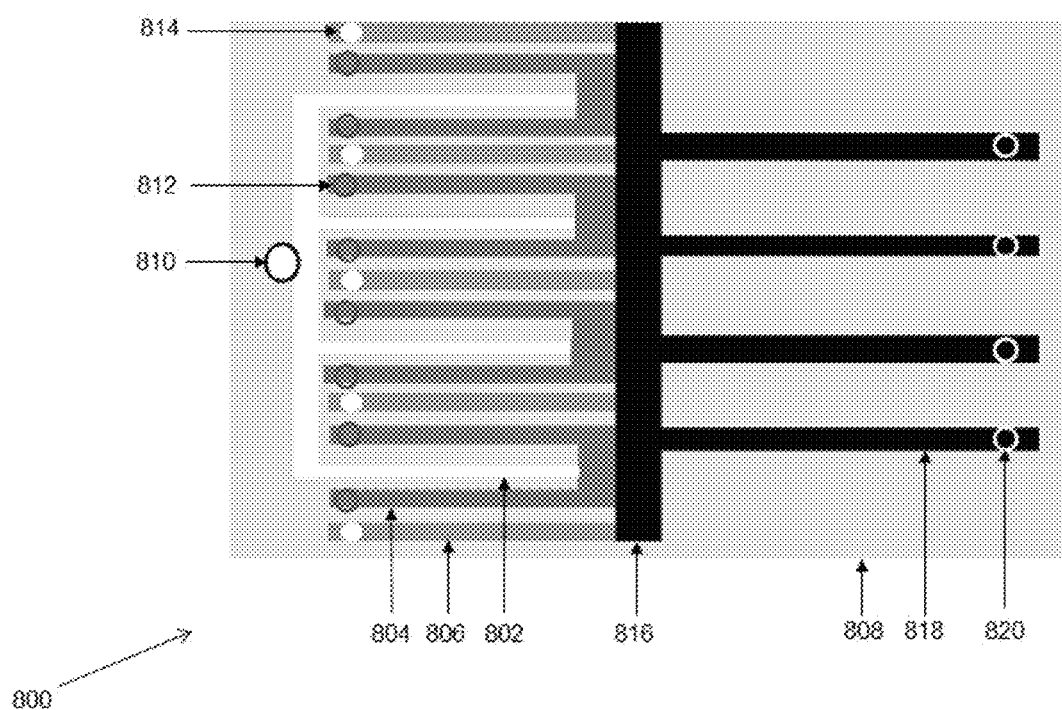
FIG. 8 illustrates a simplified cross-sectional view of a microfluidic device in accordance with another embodiment of the present application.

Reference will now be made to FIG. 8, which illustrates a microfluidic device 800 in accordance with another embodiment of the present application.

Microfluidic device 800 can have a desired dimension and shape. For example, ratio of length:breadth:height of microfluidic device 100 can be 6:3:0.5 and the cross section of microfluidic device 800 can be square or rectangular. The shape/dimension of microfluidic device 800 can be determined based on one or more parameters such as, but not limited to, type of micro-fluids to produce, desired production rate, flow rates and fabrication technique used.

Microfluidic device 800 comprises a plurality of parallel inlet channels. The plurality of parallel inlet channels comprise a first set of inlet channels 802 (hereafter first set 802) for introducing a first fluid at a first flow rate, a second set of inlet channels 804 (hereafter second set 804) for introducing a second fluid at a second flow rate and a third set of inlet channels 806 (hereafter third set 806) for introducing a third fluid at a third flow rate. The first fluid, the second fluid and the third fluid can be determined based on the type of micro-fluids to produce. Further, the first flow rate, the second flow rate and the third flow rate can be determined based on one or more parameters such as, but not limited to, desired production rate, type of micro-fluids to produce and fluid characteristics.

The plurality of parallel inlet channels can be created on a wafer 808 as illustrated in FIG. 8. Wafer 808 can have one or more characteristics such as, shape, dimension and material similar to that of wafer 104 (described in detail in conjunction with description of FIGS. 1-4). Alternately, the plurality of parallel inlet channels can be provided as separate pipe-liked channels connected using appropriate connecting members.

In accordance with the embodiment illustrated in FIG. 8, each channel of first set 802 is enclosed between two adjacent channels of second set 804. Further, each channel of second set 804 is located between two adjacent channels of third set 806. In addition, each channel of third set 806 is located at an end of the plurality of parallel inlet channels or between two adjacent channels of second set 804.

Each of first set 802, second set 804 and third set 806 can have a desired number of channels. For example, first set 802, second set 804 and third set 806 can have four, eight and five channels respectively as illustrated in FIG. 8. The number of channels in each of first set 804, second set 806 and third set 808 can be determined based on one or more parameters such as desired production rate, flow rates, type of micro-fluids to produce and fluid characteristics.

Further, each channel of first set 802, each channel of second set 804 and each channel of third set 806 can have a desired shape and dimension. For example:

Each channel of first set 802 can have a rectangular cross section and a length of 1.2X mm, a width of 4X μm and a height of 0.3X μm; and Each channel of second set 804 can have a rectangular cross section and a length of X to 2X mm, a width 7X to 10X μm and a height of 0.25X to 0.5X μm; and Each channel of third set 806 can have a rectangular cross section and a length of X to 2X mm, a width of 4X to 9X μm and a height of 0.25X to 0.5X μm; wherein X is a positive integer.

The shape/dimensions of each channel can be determined based on one or more parameters such as, but not limited to, desired production rate, flow rate, type of micro-fluids to produce and fluid characteristics.

Each of first set 802, second set 804 and third set 806 can have one or more inlets for injecting the first fluid at the first flow rate, the second fluid at the second flow rate and the third fluid at the third flow rate, respectively.

Further, each channel of a set can have a common inlet or separate inlets such as an inlet 810, one or more inlets similar to an inlet 812 and one or more inlets similar to an inlet 814 as illustrated in FIG. 8. It should be apparent that each channel of first set 802 can have a separate inlet as opposed to a common inlet. Similarly, channels of second set 804 can have a common inlet as opposed to a separate inlet. Likewise, channels of third set 806 can have a common inlet as opposed to a separate inlet. Further, each inlet can have a desired shape/dimension. For example, diameter of an inlet can be 0.004X to 0.8X mm, wherein X is a positive integer.

Microfluidic device 800 further comprises an intersection 816. As illustrated in FIG. 8, each of the plurality of parallel inlet channels can be designed such that it ends at intersection 816.

Intersection 816 can also be created on wafer 808. Intersection 816 can have a desired shape. For example, intersection 816 can have a rectangular cross section as shown in FIG. 8. Such a rectangular cross-section provides a plurality of T-junctions (not illustrated in FIG. 8). The plurality of T-junctions facilitates formation of micro-fluids due to one or more principles such as gelation.

Further, intersection 816 can have a desired dimension. For example, intersection 816 can have a length of 0.1X to 0.8X mm, a width of 2.5X to 3X mm and a height of 0.25X to 0.5X μm, wherein X is a positive integer. The shape/dimensions of intersection 816 can be determined based on one or more parameters such as, channel characteristics, desired production rate, flow rates, types of micro-fluids to produce and characteristics of the first, second and third fluids.

Microfluidic device 800 further comprises a plurality of parallel outlet channels 818 that originate from intersection 816, thereby facilitating collection of micro-fluids that can be formed at intersection 816.

Plurality of parallel outlet channels 818 can also be created on wafer 808. Alternately, plurality of parallel outlet channels 818 can be provided as separate pipe-like components connected with intersection 816.

Plurality of parallel outlet channels 818 can have a desired number. For example, the number of channels can be four as illustrated in FIG. 8. The number of channels in plurality of parallel outlet channels 818 can be determined based on one or more parameters such as, but not limited to, inlet channel characteristics, desired production rate, flow rates and types of micro-fluids to produce.

Further, each channel of plurality of parallel outlet channels 818 can have a desired shape for circulating the micro-fluids. For example, each channel can be cylindrical. Alternately, each channel can be rectanguloidal or paralleloidal in shape. Further, each channel can be made from an appropriate material.

Further, each channel of plurality of parallel outlet channels 818 can have a desired dimension. For example, each channel of plurality of parallel outlet channels 818 can have a width of 7X to 10X μm, a length of 4X to 8X mm and a height of 0.25X to 0.5X μm, wherein X is a positive integer.

In addition, each channel of plurality of parallel outlet channels 818 can have two widths. For example the first width can be 2X to 3X μm, while the second width can be 7X to 10X μm.

The shape/dimension of each channel can be determined based on one or more parameters such as, but not limited to, inlet channel characteristics, desired production rate, flow rates and types of micro-fluids to produce.

Plurality of parallel outlet channels 818 comprises one or more outlets for collecting micro-fluids. For example, plurality of parallel outlet channels 818 can have one common outlet. Alternately, each of plurality of parallel outlet channels 818 can have an outlet such as an outlet 820 as illustrated in FIG. 8.

Further, each outlet can have a desired shape/dimension. For example, a diameter of outlet 820 can be 0.007X to 0.01X mm, wherein X is a positive integer. The shape/dimension of each outlet can be determined based on one or more parameters such as, but not limited to, inlet/outlet channel characteristics, desired production rate, flow rates and types of micro-fluids to produce.

Optionally, microfluidic device 800 comprises a cover (not illustrated in FIG. 8), which can enclose the plurality of parallel inlet channels, intersection 816 and plurality of outlet channels 818 in order to facilitate the production of micro-fluids. The cover can be bonded on wafer 808 using one or more techniques such as, but not limited to, anodic bonding.

The type of material used for preparing the cover can be determined based on one or more parameters, such as, but not limited to, desired characteristics of microfluidic device 800 and desired visibility for fluid flows and micro-fluid formation. Accordingly, if visibility is desired, a material such as glass can be used for preparing the cover.

The shape/dimensions of the cover can be similar to that of wafer 808. Alternatively, the cover can have other suitable dimensions.

Microfluidic device 800 can be utilized for producing various types of micro-fluids.

Figure 9:
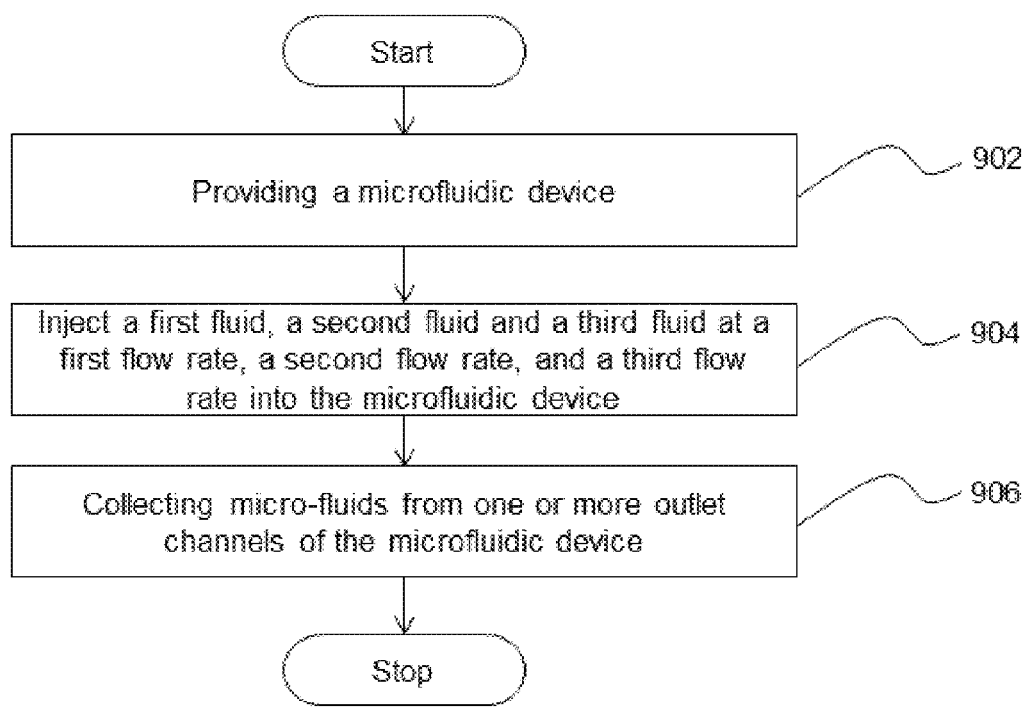
FIG. 9 illustrates a flow chart of a method for producing micro-fluids in accordance with another embodiment of the present application.

FIG. 9 illustrates a flow chart of a method for producing micro-fluids in accordance with another embodiment of the present application.

At 902, microfluidic device 800 is provided for producing micro-fluids. Providing microfluidic device 800 can include one or more of, but not limited to, fabricating microfluidic device 800 (described in detail in FIG. 10) and utilizing a pre-fabricated microfluidic device 800. In addition, providing microfluidic device 800 comprises determining a configuration of microfluidic device 800. The configuration of microfluidic device 800 can be determined based on one or more parameters such as, but not limited to, type of micro-fluids to produce, characteristics of the first, second and third fluids and desired production rate. Further, determining the configuration can include determining one or more of, but not limited to, material, shape, number and dimension of microfluidic device 800 or components thereof.

At 904, a first fluid, a second and a third fluid are injected into first set 802, second set 804 and third set 806 respectively. Here, the first fluid, the second fluid and the third fluid are injected via one or more inlets of first set 802, second set 804 and third set 806 respectively.

The first fluid, the second fluid and the third fluid to inject can be determined based on the type of micro-fluids being produced. For example, to produce core-shell controlled mono-dispersed micro-fluids, the first fluid injected can be a core, the second fluid injected can be a polymeric shell and the third fluid injected can be a cross-linker. In accordance with the example, the core can be one of, but not limited to, drugs, lipids, adhesives, pesticides essential oils, materials and dyes. Further, the polymeric shell can be one of, but not limited to, polymers containing 3-hydroxy valerate and its derivatives, cellulose and its derivatives, polymers containing 3-hydroxy butyrate and its derivatives, agarose and its derivatives, starch derivatives, alginate and its derivatives, pectin and its derivatives and chitosan and its derivatives. In addition, the cross-linker can be one of, but not limited to, calcium chloride, sodium tripolyphosphate, glutaraldehyde, ethylene glycol diglycidyl ether, imidoester cross-linker dimethyl suberimidate, N-Hydroxysuccinimide-ester cross-linker BS3 and formaldehyde. It will be apparent that the examples listed above are merely representative and numerous other types of cores, shells and cross-linkers can be utilized for preparing core-shell micro-fluids.

The first fluid, the second fluid and the third fluid are injected at a first flow rate, a second flow rate and at a third flow rate respectively. The flow rates of the first fluid, the second fluid and the third fluid can be determined based on one or more parameters such as, but not limited to, production rate and type of micro-fluids.

It should be apparent that the flow rates of any of the first fluid, the second fluid and the third fluid can be adjusted dynamically to obtain a desired output. Further, the flow rates can be identical or different.

Injecting the first fluid, the second fluid and the third fluid (hereafter referred to as three fluids) causes the three fluids to flow separately through the corresponding channels and intersect at intersection 816 and produce micro-fluids. The production of micro-fluids can be governed by one or more parameters such as, but not limited to, type of fluids, flow rates, channel characteristics and intersection characteristics.

Assuming microfluidic device 800 is utilized for producing core-shell controlled mono-dispersed micro-beads and has a configuration as illustrated in FIG. 8. In this configuration, intersection 816 facilitates gelation, wherein the core firstly meets the shell to produce core-shell particles. The core-shell particles then get cross-linked at the plurality of T-junctions to produce micro-beads. Gelation arises when the polymer drop comes into contact with the solution of the cross linker divalent ions and continues until the physical cross linking of the whole micro-fluids, where divalent ions diffusion occurs from the continuous phase across the boundary of the drop.

The micro-fluids produced at intersection 816 flow out through plurality of parallel outlet channels 818. It would be apparent that the characteristics of channels of plurality of parallel outlet channels 818 can affect the production of the micro-fluids. In accordance with the above example of core-shell controlled mono-dispersed micro-beads, the configuration of first set 802, second set 804, third set 806, intersection 816 and plurality of parallel outlet channels 818 causes the micro-beads to be core-shell controlled and mono-dispersed.

At 906, the micro-fluids are collected through plurality of parallel outlet channels 818. The micro-fluids can be collected through one or more outlets of plurality of parallel outlet channels 818.

Microfluidic device 800 can be fabricated using various techniques.

Figure 10:
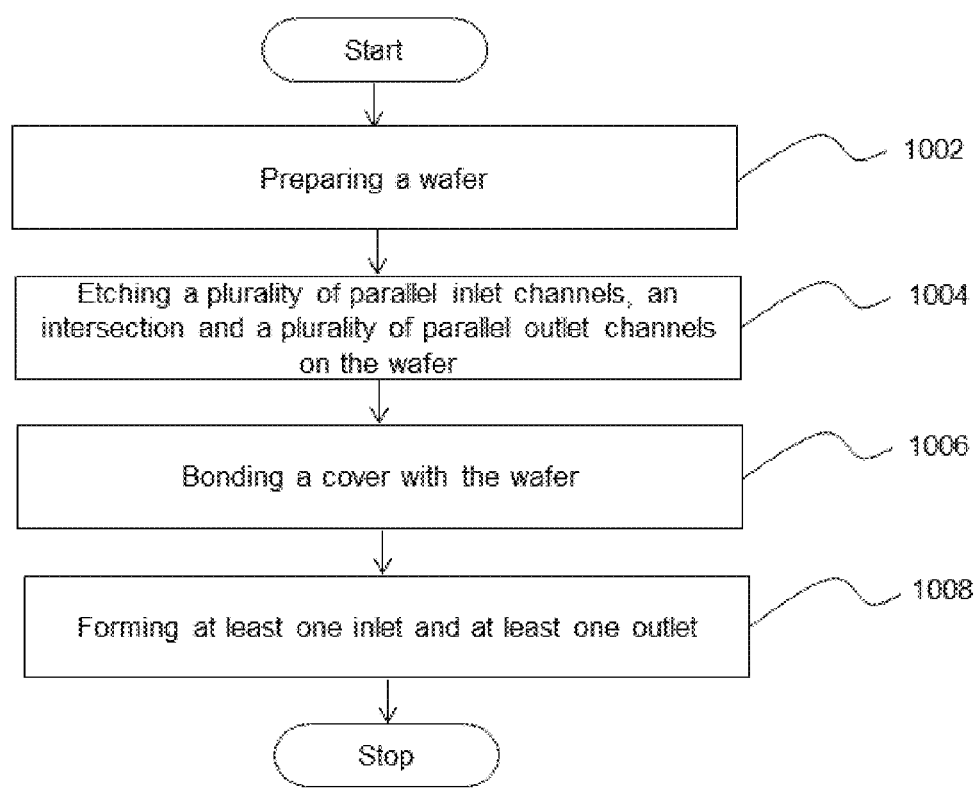
FIG. 10 illustrates a flow chart of a method for fabricating a microfluidic device in accordance with another embodiment of the present application.

FIG. 10 illustrates a flow chart of a method for fabricating microfluidic device 800 in accordance with an embodiment of the present application.

At 1002, wafer 808 is prepared. Preparing wafer 808 can include selecting one or more wafer characteristics such as, but not limited to, shape, dimension and material of wafer 808. The one or more wafer characteristics can be determined based on one or more of, but not limited to, type of micro-fluids to produce, desired production rate, flow rates and desired micro-fluid characteristics.

At 1004, a plurality of parallel inlet channels, intersection 816 and plurality of parallel outlet channels 818 are etched on wafer 808, wherein the plurality of parallel inlet channels comprises first set 802, second set 804 and third set 806. The plurality of parallel inlet channels, intersection 816 and plurality of parallel outlet channels 818 are described in detail in conjunction with description of FIG. 8.

The plurality of parallel inlet channels, intersection 816 and plurality of parallel outlet channels 818 are etched using deep reactive ion etching or other suitable etching techniques. Further, the plurality of parallel inlet channels, intersection 816 and plurality of parallel outlet channels 818 can be etched together or in separate runs.

The etching can be performed based on one or more parameters such as, but not limited to, desired shape, number, dimension and/or material of the plurality of parallel inlet channels, intersection 816 and plurality of parallel outlet channels 818.

At 1006, a cover is bonded on to wafer 808. The cover is bonded such that the cover can enclose the plurality of parallel inlet channels, intersection 816 and plurality of parallel outlet channels 818 for producing micro-fluids.

The cover can be anodically bonded on wafer 808. Alternately, any other suitable bonding technique can be utilized for bonding the cover.

The cover can be bonded on wafer 808 based on one or more cover characteristics such as, but not limited to, shape, dimension and material of the cover. The material of the cover can be glass to permit visibility during production of micro-fluids.

At 1008, one or more inlets and one or more outlets are formed. The one or more inlets and the one or more outlets can be formed on the backside of wafer 808. Further, the one or more inlets and the one or more outlets can be formed by drilling.

The one or more inlets are formed such that each of first set 802, second set 804 and third set 806 comprises one or more inlets (described in detail in conjunction with description of FIG. 8).

Further, the one or more inlets are formed based on one or more parameters such as, but not limited to, shape, dimension and material of the cover, desired flow rates, desired production rate and type of micro-fluids.

Forming the one or more inlets comprises determining the number of inlets for each of first set 802, second set 804 and third set 806 and the location of the corresponding inlets. In addition, forming the one or more inlets comprises determining one or more of, a shape and a dimension of the one or more inlets.

The one or more outlets are formed such that each of plurality of parallel outlet channels 818 comprises one or more outlets (described in detail in conjunction with description of FIG. 8). The process of forming the one or more outlets is similar to that of forming the one or more inlets. Here, the parameters to determine can include, but need not be limited to, number, shape, dimension and location of the outlets.

Various embodiments of the methods and devices described herein provide particle size control and reproducibility required for producing micro-fluids such as drug delivery particles. The methods and devices facilitate the formulation of therapeutics such as reproducible core-shell microfluid particles, increasing specificity of extracellular polymeric shell and providing controlled release of the desired core loading material. These advantages can help in the oral administration of several therapeutic proteins, i.e. insulin, by protecting the core protein from pH fluctuations along the gastrointestinal tract and also its proteases that digest 94-98% of the orally administered proteins. Moreover, the well-knit resulted micro-fluids provide effective surface functionality of the beads, which is required for the selectivity of some compounds, i.e. anti-cancer drugs, in order to prevent harmful effect of them on healthy cells. Also, immobilized living cells can produce growth factors and hormones. These types of applications require accurate control over both cell density and beads formation. The methods and devices disclosed herein can provide control over the cell density through the first set of inlet channels, which delivers the cellular load inside the shell without surface wasting. Likewise, the methods and devices disclosed herein can facilitate the production of micro-fluids by increasing their mechanical strength and the transportation ability of nutrients and oxygen due to the coherent and unmixed shell layer.

Those skilled in the art will realize that the above recognized advantages and other advantages described herein are merely exemplary and are not meant to be a complete rendering of all of the advantages of the various embodiments of the present application.

In the foregoing specification, specific embodiments of the present application have been described. However, one of ordinary skill in the art appreciates that various modifications and changes can be made without departing from the scope of the present application as set forth in the claims below. Accordingly, the specification and figures are to be regarded in an illustrative rather than a restrictive sense, and all such modifications are intended to be included within the scope of the present application. The benefits, advantages, solutions to problems, and any element(s) that may cause any benefit, advantage, or solution to occur or become more pronounced are not to be construed as critical, required, or essential features or elements of any or all of the claims. The present application is defined solely by the appended claims including any amendments made during the pendency of this application and all equivalents of those claims as issued.

What is claimed is:

1. A microfluidic device for producing micro-fluids comprising:
   a plurality of parallel inlet channels comprising a first set of inlet channels for introducing a first fluid at a first flow rate, a wafer comprising a second set of inlet channels for introducing a second fluid at a second flow rate and a third set of inlet channels for introducing a third fluid at a third flow rate, wherein each inlet channel of the second set of inlet channels is located between two channels of the third set of inlet channels;
   a mobile comb structure comprising the first set of inlet channels, wherein the first set of inlet channels is configured to move relative to the second set of channels so as to coaxially align the first set of inlet channels with the second set of inlet channels for producing micro-fluids, wherein the coaxial alignment of each channel of the first set of inlet channels is enclosed within a corresponding channel of the second set of channels;

an intersection disposed at an end of the plurality of parallel inlet channels, wherein the intersection is configured to facilitate formation of micro-fluids; and a plurality of parallel outlet channels originating from the intersection, wherein the plurality of parallel outlet channels is configured to facilitate collection of the micro-fluids.

2. The microfluidic device of claim 1 further comprising a wafer, wherein the second set of inlet channels, the third set of inlet channels, the intersection and the plurality of outlet channels are etched on the wafer of the microfluidic device.

3. The microfluidic device of claim 2 further comprising a glass cover, wherein the glass cover is bonded with the wafer such that the glass cover is configured to enclose the plurality of inlet channels, the intersection and the plurality of outlet channels.

4. The microfluidic device of claim 1, wherein each inlet channel of the first set of inlet channels is a Polyether ether ketone (PEEK) capillary tube.

5. The microfluidic device of claim 1, wherein each of the first set of inlet channels, the second set of inlet channels and the third set of inlet channels comprises at least one inlet.

6. The microfluidic device of claim 5, wherein the at least one inlet comprises a diameter of 0.004X to 0.8X mm, wherein X is a positive integer.

7. The microfluidic device of claim 5, wherein the first set of inlet channels comprises an inlet for injecting the first fluid at the first flow rate, wherein each inlet channel of the second set of inlet channels comprises an inlet for injecting the second fluid at the second flow rate and wherein each inlet channel of the third set of inlet channels comprises an inlet for injecting the third fluid at the third flow rate.

8. The microfluidic device of claim 1, wherein the plurality of parallel outlet channels comprises at least one outlet for collecting the micro-fluids.

9. The microfluidic device of claim 8, wherein the at least one outlet comprises a diameter of 0.007X to 0.01X mm, wherein X is a positive integer.

10. The microfluidic device of claim 8, wherein each of the plurality of parallel outlet channels comprises an outlet for collecting the micro-fluids.

11. The microfluidic device of claim 1, wherein the first set of inlet channels comprises five channels, wherein the second set of inlet channels comprises five channels and wherein the third set of inlet channels comprises six channels.

12. The microfluidic device of claim 1, wherein each of the first set of inlet channels is 3X μm to 5X μm in width, each of the second set of inlet channels is 7X to 10X μm in width and each of the third set of inlet channels is 4X to 9X μm in width, wherein X is a positive integer.

13. The microfluidic device of claim 1, wherein the plurality of parallel outlet channels comprises five channels.

14. The microfluidic device of claim 1, wherein each of the plurality of parallel outlet channels comprises a first width of 2X to 3X μm and a second width of 7X to 10X μm, wherein X is a positive integer.

15. The microfluidic device of claim 1, wherein the ratio of length:breadth:height of the microfluidic device is 6:3:0.5.

16. The microfluidic device of claim 15, wherein the height of a wafer of the microfluidic device is equal to the height of a glass cover of the microfluidic device.

17. The microfluidic device of claim 15, wherein the ratio of the length:width:height of the mobile comb structure is 1.5:3:0.25.

18. The microfluidic device of claim 15, wherein the ratio of the length of plurality of parallel inlet channels:the length of the intersection:the length of the plurality of parallel outlet channels is 1.2:0.5:6.

19. The microfluidic device of claim 18, wherein the intersection is box shaped and comprises a length:width:height ratio of 800:3000:0.5.

20. The microfluidic device of claim 1, wherein the diameter of the micro-fluids is in the range of X to 5X μm, wherein X is a positive integer.

21. A method for producing micro-fluids, the method comprising:

providing a microfluidic device comprising:
a plurality of parallel inlet channels comprising a first set of inlet channels for introducing a first fluid at a first flow rate, a wafer comprising a second set of inlet channels for introducing a second fluid at a second flow rate and a third set of inlet channels for introducing a third fluid at a third flow rate, wherein each inlet channel of the second set of inlet channels is located between two channels of the third set of inlet channels;

a mobile comb structure comprising the first set of inlet channels, wherein the first set of channels is configured to move relative to the second set of channels so as to coaxially align the first set of inlet channels with the second set of inlet channels for producing micro-fluids, wherein the coaxial alignment of each channel of the first set of inlet channels is enclosed within a corresponding channel of the second set of channels;

an intersection disposed at an end of the plurality of parallel inlet channels, wherein the intersection is configured to facilitate formation of micro-fluids; and a plurality of parallel outlet channels originating from the intersection, wherein the plurality of parallel outlet channels is configured to facilitate collection of the micro-fluids;

injecting the first fluid into the first set of inlet channels at the first flow rate, the second fluid into the second set of inlet channels at the second flow rate and the third fluid into the third set of inlet channels at the third flow rate, thereby causing the first fluid, the second fluid and the third fluid to intersect at the intersection and form micro-fluids, wherein the micro-fluids flow out from the intersection into the plurality of parallel outlet channels; and collecting the micro-fluids from the plurality of parallel outlet channels.

22. The method of claim 21, wherein the first fluid is a sample, the second fluid is a polymer and the third fluid is a cross-linker.

23. The method of claim 22, wherein the micro-fluids are core-shell controlled cross-linked mono-dispersed micro-fluids.

24. The method of claim 23 wherein the formation of the core-shell controlled cross-linked mono-dispersed micro-fluids comprises:

formation of core-shells in response to intersection of the sample with the polymer; and structuring the core-shells in response to intersection of the core-shells with the cross-linker to form the core-shell controlled cross-linked mono-dispersed micro-fluids.

25. The method of claim 21, wherein the first flow rate is F μL/min, the second flow rate is 2F μL/min and the third flow rate is 3F μL/min, wherein F is a positive integer.

26. The method of claim 21 further comprising replacing the mobile comb structure with a similar mobile comb structure, wherein the similar mobile comb structure comprises a fourth set of inlet channels similar to the first set of inlet channels, wherein channels of the fourth set of inlet channels comprise a different inner diameter in comparison to channels of the first set of inlet channels.

27. The method of claim 26, wherein the size of microfluids is controlled by utilizing the similar mobile comb structure.

28. A method for fabricating a microfluidic device for producing micro-fluids, the method comprising:

fabricating a mobile comb structure configured to move relative to a wafer, the mobile comb structure comprising a first set of inlet channels for introducing a first fluid at a first flow rate, wherein channels of the first set of inlet channels are parallel to each other, wherein fabricating the mobile comb structure comprises forming the first set of inlet channels connected to a fluid routing component, wherein the fluid routing component comprises an inlet for injecting a first fluid at a first flow rate;

preparing the wafer;

etching a plurality of parallel inlet channels, an intersection and a plurality of parallel outlet channels in the wafer;

wherein the plurality of parallel inlet channels comprises a second set of inlet channels for introducing a second fluid at a second flow rate and a third set of inlet channels for introducing a third fluid at a third flow rate, wherein the second set of inlet channels is configured to permit movement of the first set of inlet channels with respect to the second set of inlet channels so as to coaxially align the first set of inlet channels with the second set of inlet channels for producing micro-fluids, wherein the coaxial alignment of each channel of the first set of inlet channels is enclosed within a corresponding channel of the second set of inlet channels and the first set of inlet channels and the second set of inlet channels terminate at the intersecting region, wherein each inlet channel of the second set of inlet channels is located between two adjacent inlet channels of the third set of inlet channels, and wherein each channel of the third set of inlet channels is located at one of an end of the plurality of parallel inlet channels and in between two adjacent channels of the second set of inlet channels;

wherein the intersection is disposed at an end of the plurality of parallel inlet channels, wherein the intersection is configured to facilitate formation of micro-fluids; and wherein the plurality of parallel outlet channels originates from the intersection, wherein the plurality of parallel outlet channels is configured to facilitate collection of the micro-fluids;

bonding a cover with the wafer, wherein the cover is configured to enclose the plurality of parallel inlet channels, the intersection, the plurality of parallel outlet channels and the mobile comb structure;

forming at least one inlet for each of the first set of inlet channels and the second set of inlet channels and at least one outlet for the plurality of parallel outlet channels; and integrating the mobile comb structure with the wafer.

29. The method of claim 28, wherein the wafer is a silicon wafer.

30. The method of claim 28, wherein the plurality of parallel inlet channels, the intersection and the plurality of parallel outlet channels are etched using deep reactive ion etching.

31. The method of claim 28, wherein the cover is a glass cover.

32. The method of claim 31, wherein the glass cover is anodically bonded with the wafer.